United States Patent [19]

Stegmann et al.

[11] Patent Number: 4,921,966
[45] Date of Patent: May 1, 1990

[54] PROCESS FOR THE PREPARATION OF LIQUID MIXTURES OF ALKYLATED 2-(2-HYDROXYPHENYL)BENZOTRIAZOLES

[75] Inventors: Werner Stegmann, Liestal; Reto Luisoli, Hölstein, both of Switzerland

[73] Assignee: Ciba-Geigy Corporation, Ardsley, N.Y.

[21] Appl. No.: 284,265

[22] Filed: Dec. 14, 1988

[30] Foreign Application Priority Data

Dec. 23, 1987 [CH] Switzerland ............... 5034/87

[51] Int. Cl.$^5$ ..................................... C07D 249/20
[52] U.S. Cl. ......................................... 548/260
[58] Field of Search ................ 548/257, 260, 261

[56] References Cited

U.S. PATENT DOCUMENTS

| | | | |
|---|---|---|---|
| Re. 29,546 | 3/1978 | Strobel | 548/260 |
| 3,004,896 | 10/1961 | Heller et al. | |
| 3,055,896 | 9/1962 | Boyle et al. | |
| 3,072,585 | 1/1963 | Millonis et al. | |
| 3,074,910 | 1/1963 | Dickson, Jr. | |
| 3,159,646 | 12/1964 | Millionis et al. | 548/260 |
| 3,189,615 | 6/1965 | Heller et al. | 548/260 |
| 3,230,194 | 1/1966 | Boyle et al. | 548/260 |
| 3,399,173 | 8/1968 | Heller | 548/173 |
| 3,983,132 | 9/1976 | Strobel | 548/260 |
| 4,096,242 | 6/1978 | Strobel | |
| 4,129,521 | 12/1978 | Strobel | |
| 4,278,590 | 7/1981 | Dexter et al. | |
| 4,283,327 | 8/1981 | Dexter et al. | |
| 4,383,863 | 5/1983 | Dexter et al. | 548/260 |
| 4,587,346 | 5/1986 | Winter et al. | 548/260 |
| 4,675,352 | 6/1987 | Winter et al. | 548/260 |
| 4,845,180 | 7/1989 | Henry et al. | 548/260 |

FOREIGN PATENT DOCUMENTS 0057160 8/1982 European Pat. Off. .

OTHER PUBLICATIONS

Chem. Abstracts vol. 102, entry 95578f, (1985).

*Primary Examiner*—Donald G. Daus
*Attorney, Agent, or Firm*—Luther A. R. Hall

[57] ABSTRACT

A process for the preparation of a mixture of 2-(2-hydroxyphenyl)benzotriazole which is liquid at room temperature by alkylating 2-(2-hydroxy-5-methylphenyl)benzotriazole with a $C_8$-$C_{14}\alpha$-olefin in the melt at elevated temperature, in the presence of sulfonic acid as catalyst, comprising using not less than 0.5 mol of the acid catalyst and 1.5-3 mol of α-olefin per mol of 2-(2-hydroxy-5-methylphenyl)benzotriazole, carrying out the alkylation in the temperature range from 165° to 190° C., separating the crude product phase upper phase) from the sulfonic acid phase, and working up said crude product phase by distillation by means of a thin-film evaporator, a thin-film evaporator fitted with a distillation column, or a short path distillation apparatus.

16 Claims, No Drawings

PROCESS FOR THE PREPARATION OF LIQUID MIXTURES OF ALKYLATED 2-(2-HYDROXYPHENYL)BENZOTRIAZOLES

The present invention relates to an improved process for the preparation of liquid mixtures of isomers of 2-(2-hydroxyphenyl)benzotriazoles by alkylating 2-(2-hydroxy-5-methylphenyl)benzotriazole with $C_8$–$C_{14}$ α-olefins, and to the mixtures obtainable by said process.

UV Absorbers of the 2-(2-hydroxyphenyl)benzotriazole series have long been known as very effective light stabilisers for a very wide range of organic materials and are well established on the market. Examples of such UV absorbers, their preparation and utilities are disclosed, for example, in U.S. Pat. specifications 3 004 896, 3 055 896, 3 072 585, 3 074 910, 3 189 615 and 3 230 194.

For many utilities, however, such benzotriazoles have only limited compatibility and exhibit a tendency to exudation, sublimation and/or volatilisation, for example even when processing must be effected at elevated temperatures. To improve these properties, modifications have been made to the substitution pattern of the cited benzotriazoles. Reference is made in this connection to U.S. patent specifications 4 283 327, 4 278 590 and 4 383 863.

For the reasons mentioned above, the search for 2-(2-hydroxyphenyl)benzotriazoles which are liquid at room temperature has recently been intensified, as these compounds in particular also have advantages when incorporated in specific substrates, for example photographic materials. Reference is made in this connection to U.S. patent specifications 3 983 132, 4 096 242 and 4 129 521 and to European published patent application A 57 160.

Mixtures of isomers of higher alkylated 2-(2-hydroxy-5-methyl-phenyl)benzotriazoles and a process for the preparation thereof are disclosed in U.S. patent specifications 4 587 346 and 4 675 352. These mixtures are liquid at room temperature and exhibit a number of outstanding properties when incorporated in the various substrates cited in these two patent specifications. The preparatory process described therein in some respects does not fully meet the requirements made of a large-scale production of the products in question. Hence there is a need to provide a simple, cost-effective process which can be carried out on a large scale and which is able to give the products in high yield and good purity.

A process has now been found that meets these requirements and affords the product in surprisingly high purity and yield. The solution of the problem has been achieved by maintaining specific reaction parameters during the alkylation in conjunction with a special method of working up the reaction mixture.

The process of this invention for the preparation of a mixture of 2-(2-hydroxyphenyl)benzotriazoles which is liquid at room temperature by alkylating 2-(2-hydroxy-5-methylphenyl)benzotriazole with a $C_8$–$C_{14}$α-olefin in the melt at elevated temperature, in the presence of sulfonic acid as catalyst, comprises using not less than 0.5 mol of the acid catalyst and 1.5–3 mol of α-olefin per mol of 2-(2-hydroxy-5-methylphenyl)benzotriazole, carrying out the alkylation in the temperature range from 165° to 190° C., separating the crude product phase (upper phase) from the sulfonic acid phase, and working up said crude product phase by distillation by means of a thin-film evaporator, a thin-film evaporator fitted with a distillation column, or a short path distillation apparatus.

Sulfonic acid is used as acid catalyst and may be an aromatic or, preferably, an aliphatic sulfonic acid, for example benzenesulfonic acid, toluenesulfonic acid such as p-toluenesulfonic acid, methanesulfonic acid or ethanesulfonic acid. For practical purposes, methanesulfonic acid is to be preferred.

The reaction temperature is preferably in the range from 170° to 180° C.

The amount of sulfonic acid catalyst is not less than 0.5 mol per mol of 2-(2-hydroxy-5-methylphenyl)benzotriazole. The upper limit of the concentration of catalyst is not crucial, as good results are obtained even with large amounts of sulfonic acid. The upper limit will be determined by economic considerations. It is therefore convenient to use 0.5–10 mol of catalyst per mol of starting material. It is preferred to use not less than 0.8 mol of sulfonic acid, for example 0.8–5 mol. The process can be carried out most expediently and economically with about 1 mol of sulfonic acid per mol of starting benzotriazole.

The preferred amount of alkylating agent (α-olefin) is in the range from 2 to 3 mol, for example from 2.2 to 2.7 mol, most preferably about 2.5 mol, per mol of 2-(2-hydroxyphenyl)benzotriazole.

Straight chain as well as branched α-olefins may be used as alkylating agents. In practice, it is convenient to use commercially available isomeric mixtures of α-olefins. As will be explained below, partial isomerisation of the alkyl chain takes place in any case during the alkylation. The alkylation is preferably carried out with $C_{10}$–$C_{24}$α-olefins, most preferably with 1-dodecene, which may be in straight chain or branched chain configuration or in the form of a mixture of isomers.

In a particularly preferred variant of the process, the alkylating agent is added continuously to the reaction mixture, for example by means of a fractionating pump. It is most preferred to run in the olefin beneath the surface of the reaction mixture. The metered addition of the alkylating agent in particular further reduces the formation of by-products such as oligomers of the α-olefin.

It is also advantageous to ensure that the reaction mixture is thoroughly mixed. To this end it is advisable to use an efficient stirrer. It is also expedient to carry out the reaction in an inert gas atmosphere, for example under nitrogen.

The reaction is carried out in the melt without the addition of an actual solvent. The α-olefin or the mixture of final products obtained from the alkylation can act as solvent or diluent.

When the alkylation is complete (the reaction time can vary, depending on the chosen reaction parameters, but is normally from half an hour to 15 hours, for example from 3 to 10 hours), the phase containing the crude product (upper phase) is separated from the two-phase reaction mixture and worked up by a specific distillation method.

Before the distillation proper, it is expedient to wash the crude product phase to remove impurities (extraction). This extraction can be performed preferably by washing the crude product phase 1 to 5 times with water or sodium bicarbonate solution. Especially preferred is extraction with the latter and subsequent extraction with water. The combined washing extracts are preferably added to the sulfonic acid phase to recover unreacted starting material (see below).

After extraction, it is advisable to decolourise the crude product phase before effecting the working up proper (distillation). This can be done by adding a conventional decolourising agent such as activated charcoal or, preferably, fuller's earth. It is also advantageous to remove residual water from the crude product phase by distillation. After clarifying filtration to remove the decolourising agent, the working up proper of the crude product can be carried out. This working up can, of course, also be carried out without the optional steps of extraction, decolourising and removal of water, i.e. the crude product phase separated from the reaction mixture can be subjected direct to distillation.

Distillation is carried out with a thin-film evaporator, a thin-film evaporator fitted with a distillation column, or a short path distillation apparatus. Residual amounts of the starting α-olefin, oligomers of the olefin formed during the reaction as by-products and, finally, residual amounts of 2-(2-hydroxy-5-methylphenyl)benzotriazole, are first separated in the distillation apparatus. The residual liquid product can be used as obtained. It is, however, expedient to subject the product to distillation for further purification in the same or in another distillation apparatus of the described kind. A very pure product is obtained in this manner.

To make the process still more economical, it is advantageous to recover unreacted starting benzotriazole from the reaction mixture and to reuse it in the alkylation. To this end, the bulk of unreacted 2-(2-hydroxy-5-methylphenyl)benzotriazole present in the sulfonic acid phase (lower phase) separated from the crude product phase is precipitated by controlled crystallisation, preferably by dilution with water and/or by diluting the washing extracts from the extraction of the crude product phase, if performed. Precipitation can also be effected by neutralising the sulfonic acid phase, or said phase can also be neutralised before it is diluted. The precipitated starting benzotriazole can be isolated by filtration in conventional manner, washed until neutral and, if desired or necessary, dried, and subsequently reused for the next alkylation batch, in which case drying is not absolutely necessary.

The first distillate obtained from the distillation of the crude product phase likewise contains starting benzotriazole that can also be precipitated by crystallisation, for example by cooling, preferably to ca. 0° C. After isolation by filtration, washing and, if desired or necessary, drying, the product can also be returned to the alkylation.

The following schematic showing a preferred embodiment of the process (with recovery of the starting material) will serve to illustrate the process of the invention further:

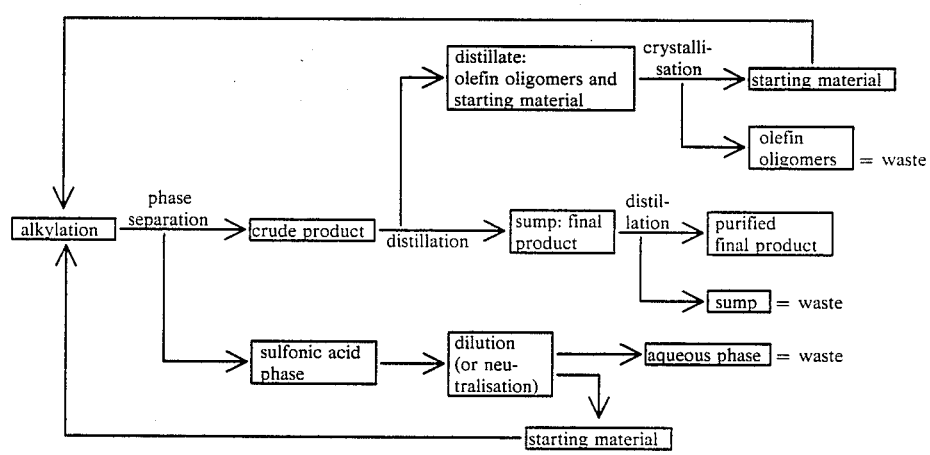

starting material = 2-(2-hydroxy-5-methylphenyl)benzotriazole
final product = mixture of isomers of compounds of formula I In a further preferred embodiment of the process, especially if methanesulfonic acid is used as catalyst, the reaction mixture is diluted with water. The ratio of water:sulfonic acid in the dilute reaction mixture can vary within wide limits and is in the range from 0.5:1 to 1:10, for example from 0.8:1 to 1:5, and is preferably about 1:1. The consequence of diluting the reaction mixture with water is that almost the entire residual amount of 2-(2-hydroxy-5-methylphenylbenzotriazole transfers from the sulfonic acid phase to the crude product phase. Phase separation and working up of the crude product phase are effected as described above. The separated aqueous sulfonic acid phase is then conveniently worked up by distillation, for example in 3 steps, comprising removing the bulk of the water in a first step, separating dilute methanesulfonic acid (which is conveniently returned to the distillation) in a second step, and distilling pure methanesulfonic acid in a third step. This latter product can be readily reused for a fresh alkylation batch. This process variant makes it possible, on the one hand, to dispense with the step of recovering unreacted starting benzotriazole from the sulfonic acid phase and, on the other, to recycle the sulfonic acid almost completely. This process can be illustrated, for example, by the following scheme:

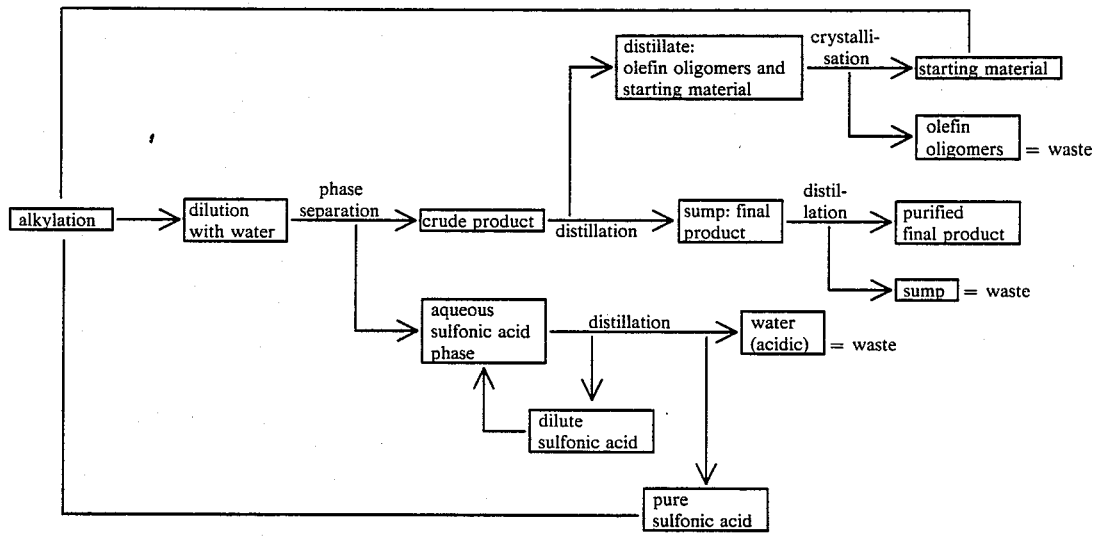

The starting 2-(2-hydroxy-5-methylphenyl)benzotriazole is known and is a commercially available UV absorber.

The invention further relates to the liquid mixtures of alkylated 2-(2-hydroxy-5-methylphenyl)benzotriazole obtainable by the process of this invention.

The liquid mixtures of alkylated 2-(2-hydroxyphenyl)benzotriazole are useful light stabilisers which can be incorporated in numerous substrates to protect them from light-induced degradation. Examples of such potential applications will be found in U.S. patent specifications 4 587 346 and 4 675 352. The liquid mixtures are used with particular advantage in lacquer systems and, most particularly, in photographic materials.

As already mentioned, the products obtainable in this invention are mixtures of compounds. The products contain mainly alkylation products of formula

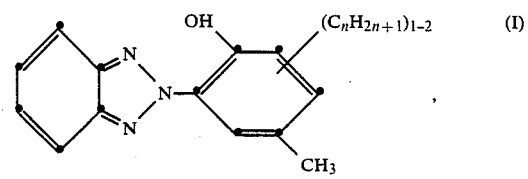

wherein n is an integer from 8 to 14 and the alkyl radical is a mixture of at least two, preferably at least three, isomeric radicals. One or two alkyl radicals are introduced by the alkylation. The main components contain only one long-chain alkyl radical which, in turn, is naturally a mixture of at least two isomers. Preferably n is 10 to 14 and, most preferably, is 12.

The long-chain alkyl radical or radicals introduced in the alkylation are a random mixture of two or more isomeric alkyl chains. Apart from the fact that a mixture of isomers can be used as α-olefin, isomerisation of the alkyl chain occurs at all events in the course of the alkylation. In particular, the attachment of the α-olefin through the 1-position or 2-position takes place. In the former case, an α-unbranched alkyl results and, in the latter case, an α-branched alkyl results.

A long-chain alkyl radical in formula I is preferably in 3-position of the phenyl ring (ortho to the OH group). The mixture of this invention can, however, also contain insignificant amounts of other reaction products that are not covered by formula I. For example, traces of alkylation can also take place in the benzene nucleus of the benzotriazole ring, especially alkylation with short-chain fission products of the olefin. Said benzene nucleus can thus contain, for example, one or more alkyl groups of less than 8 carbon atoms. The phenol ring can be substituted to a very insignificant degree by such short-chain alkyl groups. On the other hand, oligomerisation of the olefin can occur in the reaction mixture. The oligomers formed, especially dimers, can likewise result in alkylation of the phenol ring, so that compounds are also formed that are substituted at this ring by alkyl chains of more than 14 carbon atoms, for example by those of 16 to 28 carbon atoms. The final product may contain compounds of this type in varying amounts, for example up to 5% and, in individual cases, up to 10%.

As already indicated, the starting olefin is oligomerised, in particular dimerised, under the reaction conditions. The oligomers are substantially removed in the course of the purifying distillation, but the product may still contain such dimers (oligomers), for example in an amount of 0.1 to 5%, in extreme cases up to 10%.

The quantitative analysis of the reaction product is exceedingly difficult, so that it is not possible to determine its exact composition.

As has already been said, a basic process for the preparation of mixtures of isomers of the type of formula I is disclosed in U.S. patent specifications 4 587 346 and 4 675 352. The process specifically disclosed therein (q.v. Examples 1–7 of these two patent specifications) gives only low yields and is not very satisfactory in practice on account of the working up by solvent extraction which is difficult to perform in large-scale production. These shortcomings can be overcome by the combination according to this invention of specific reaction parameters and a special method of working up. Moreover, it must be considered surprising that, in the distillation of the product melt, the separation of the olefin oligomers of the products of formula I can be effected so smoothly, although separation by means of other conventional distillation apparatus does not lead to this result.

The process of this invention affords not only a high yield, but also, surprisingly, products that are even more suitable for a variety of potential applications than products obtained by the known process.

The use of preferred embodiments of the process of the invention, for example the metered addition of the α-olefin, further inhibits oligomerisation of the olefin and makes it possible to reduce the excess of α-olefin. The conversion is enhanced and the residual content of starting material is lower. Taking into account the preferred recovery of unreacted starting material, yields close to 100% of theory are obtained.

The process of the invention is illustrated in more detail by the following Examples in which, as also in the foregoing description, parts and percentages are by weight, unless otherwise stated.

EXAMPLE 1

A 1.5 liter jacketed flask equipped with propeller mixer, a device for submerged metering with fractionating pump, nitrogen inlet and a distillation head attached to a water-jet pump, is charged at room temperature with 225.2 g (1 mol) of 2-(2-hydroxy-5-methylphenyl)-benzotriazole and 96.1 g (1 mol) of methanesulfonic acid, and blanketed with nitrogen. With slow stirring, the mixture is heated to 175° C., the suspension going into solution at ca. 125° C. With efficient stirring, 420.8 g (2.5 mol) of n-dodecane are run in uniformly beneath the surface of the mixture at 175° C. over 6 hours. After stirring for a further 30 minutes at 175° C., the alkylation is complete. The residual amount of unreacted 2-(b 2-hydroxy-5-methylphenyl)-benzotriazole is found to be 3-5% by thin-layer chromatography, corresponding to 15-20% of the amount originally used. After cooling to ca. 95° C., the lower phase containing methanesulfonic acid and unreacted starting benzotriazole is separated. The upper phase (crude product phase) is extracted first with 100 ml of 4% sodium bicarbonate solution and then twice with 100 ml of water. The extracts are cautiously added to the separated methanesulfonic acid phase, whereupon the dissolved 2-(2-hydroxy-5-methylphenyl)benzotriazole crystallises out and is isolated by filtration, washed until neutral and dried, affording 25 g of starting material (corresponding to 11.2%, based on the amount used).

The extracted crude product phase, after addition of 10 g of fuller's earth (Prolith Rapid ®), is completely freed from water by distillation up to 120° C./5 mbar and decolourised by clarifying filtration at 100° C. Yield: ca. 570 g of a pale yellow, clear crude product.

This crude product is then distilled on a 0.02 m² thin-film evaporator at a jacket temperature of 240° C. and a pressure of 1-3 mbar, such that the content of dodecene oligomers is lower than 2% and of 2-(2-hydroxy-5-methylphenyl)benzotriazole lower than 0.2%, determined by gas chromatography. Finally, the residue (sump, ca. 320 g) is distilled on the thin-film evaporator at a jacket temperature of 285° C. and a pressure of 1-3 mbar (head temperature: ca. 240° C.), affording the desired mixture of compounds of formula I, in which n is 12, in the form of a pale yellow liquid product with a refractive index $n^{20}_D = 1.5677$.

The distillate from the first distillation on the thin-film evaporator is cooled to 0° C. in a 350 ml sulfonating flask equipped with anchor agitator, whereupon a further 16 g (corresponding to 7% of theory, based on the amount used of 2-(2-hydroxy-5-methylphenyl)benzotriazole crystallise out and are isolated by filtration, washed and dried. The total amount of starting material recovered is therefore ca. 18% of theory, based on the amount originally used. This starting material can be used again for the next batch without a prior drying being necessary.

EXAMPLE 2

A 1.5 liter jacketed flask equipped with propeller mixer, a device for submerged metering with fractionating pump, nitrogen inlet and a distillation head attached to a water-jet pump, is charged at room temperature with 225.2 g (1 mol) of 2-(2-hydroxy-5-methylphenyl)-benzotriazole and 96.1 g (1 mol) of methanesulfonic acid, and blanketed with nitrogen. With slow stirring, the mixture is heated to 175° C., the suspension going into solution at ca. 125° C. With efficient stirring, 420.8 g (2.5 mol) of n-dodecene are run in uniformly beneath the surface of the mixture at 175° C. over 8 hours. After stirring for a further 30 minutes at 175° C., the alkylation is complete. The maximum residual amount of unreacted 2-(2-hydroxy-5-methylphenyl)-benzotriazole is found to be 3% by thin-layer chromatography, corresponding to 2-16% of the amount originally used. After cooling to ca. 90° C., 96 ml of water are added over 10 minutes. After stirring for 10 minutes at 90° C., the lower phase containing methanesulfonic acid is cautiously separated (for working up, see below). The upper phase (crude product phase) is extracted first with 100 ml of 4% sodium bicarbonate solution and then twice with 100 ml of water. The extracted crude product phase, after addition of 10 g of fuller's earth (Prolith Rapid ®), is completely freed from water by distillation up to 120° C./5 mbar and decolourised by clarifying filtration at 120° C. Yield: ca. 610 g of a pale yellow, clear crude product.

This crude product is then distilled on a 0.02 m² thin-film evaporator at a jacket temperature of 240° C. and a pressure of 1-3 mbar, such that the content of dodecene oligomers is lower than 2% and of 2-(2-hydroxy-5-methylphenyl)benzotriazole lower than 0.2%, determined by gas chromatography. Finally, the residue (sump, ca. 347 g) is distilled on the thin-film evaporator at a jacket temperature of 285° C. and a pressure of 1-3 mbar (head temperature ca. 240° C.), affording 326 g (yield=85% of theory) of the desired mixture of compounds of formula I, in which n is 12, in the form of a pale yellow liquid product with a refractive index $n^{20}_D = 1.5677$.

The distillate from the first distillation on the thin-film evaporator is cooled to 0° C. in a 350 ml sulfonating flask equipped with anchor agitator, whereupon ca. 27 g (corresponding to 12% of theory, based on the amount employed) of 2-(2-hydroxy-5-methylphenyl)-benzotriazole crystallise out and are isolated by filtration and washed. The total amount of starting material recovered is therefore ca. 12% of theory, based on the amount originally used. This starting material can be used again for the next batch without a prior drying being necessary.

A 250 ml pear-shaped flask fitted with capillary, 15 cm Vigreux column, distillation head with condenser, pig adapter and 100 ml round-bottomed flask, connected to a vacuum rotary vane pump, is charged with ca. 185 g of the separated aqueous methanesulfonic acid phase. After applying a vacuum of 100 mbar, the contents of the flask are heated until, at a bath temperature of ca. 55° C., virtually no more water distils and the head temperature falls. About 85 ml of slightly acidic water (pH>3) is separated in this way. After changing the receiver, the vacuum is corrected to ca. 2 mbar and ca. 7.5 g of methanesulfonic acid (10-20%) are distilled. This product can be reused in the next distillation. After changing the receiver again, ca. 87 g of pure methanesulfonic acid are distilled under a vacuum of ca. 2 mbar and a head temperature of ca. 125°-130° C. and a bath temperature of 155°-175° C. This methanesulfonic acid conforms to a technical product with respect to appearance (slightly brownish) and concentration (99%). The water content (0.5%) is even lower than that of commercial product. The yield is ca. 90% of the amount of methanesulfonic acid used in the alkylation.

This distillation can also be carried out in like manner in a sulfonating flask (batchwise) or continuously in a 2-step distillation apparatus.

What is claimed is:

1. An improved process for the preparation of a mixture of 2-(2-hydroxyphenyl)-benzotriazoles which is liquid at room temperature by alkylating 2-(2-hydroxy-5-methylphenyl)-benzotriazole with a $C_8$-$C_{14}$-alpha-olefin in the melt at elevated temperature, in the presence of a sulfonic acid catalyst, wherein the improvement consists essentially of
   (i) employing not less than 0.5 mol of acid catalyst and only 1.5 to 3 moles of alpha-olefin per each mole of 2-(2-hydroxy-5-methylphenyl)-benzotriazole,
   (ii) carrying out the alkylation reaction in the temperature range from 165° to 190° C.,
   (iii) separating the upper crude product phase from the lower sulfonic acid phase, and
   (iv) isolating the final product mixture by working up said crude product phase by distillation using a thin-film evaporator, a thin-film evaporator fitted with a distillation column or a short-path distillation apparatus.

2. A process according to claim 1, wherein the catalyst is methanesulfonic acid.

3. A process according to claim 1, wherein the alkylation is carried out in the temperature range from 170°-180° C.

4. A process according to claim 1, wherein not less than 0.8 mol of sulfonic acid is used per mol of 2-(2-hydroxy-5-methylphenyl)benzotriazole.

5. A process according to claim 1, wherein 2.2 to 2.7 mol of α-olefin are used per mole of 2-(2-hydroxy-5-methylphenyl)benzotriazole.

6. A process according to claim 1, wherein the alkylation is carried out with 1-dodecene.

7. A process according to claim 1, wherein the α-olefin is added continuously to the reaction mixture.

8. A process according to claim 1, wherein the reaction mixture is diluted with water before phase separation.

9. A process according to claim 1, wherein the separated crude product phase is washed (extracted) before the distillation, decolourised, and substantially freed from water by distillation.

10. A process according to claim 1, wherein the distillation proper comprises first separating unreacted starting material and oligomers of the α-olefin and subsequently purifying the product itself by distillation in an apparatus as described herein.

11. A process according to the claim 1, wherein unreacted starting benzotriazole is recovered from the separated sulfonic acid phase and recycled to the alkylation step when the reaction mixture has not been diluted before phase separation.

12. A process according to claim 11, wherein 2-(2-hydroxy-5-methylphenyl)-benzotriazole is precipitated in the sulfonic acid phase by crystallisation.

13. A process according to claim 12, wherein the crystallisation is carried out by dilution with water and/or addition of the washing extracts from the extraction of the crude product phase.

14. A process according to claim 1, wherein 2-(2-hydroxy-5-methylphenyl)benzotriazole is precipitated by crystallisation from the mixture distilled from the crude product phase.

15. A process according to claim 8, wherein the sulfonic acid is recovered after separation of the crude product phase from the aqueous sulfonic acid phase by distillation.

16. A process according to claim 1, wherein the bulk of the liquid mixture of 2-(2-hydroxyphenyl)benzotriazole consists of compounds of formula

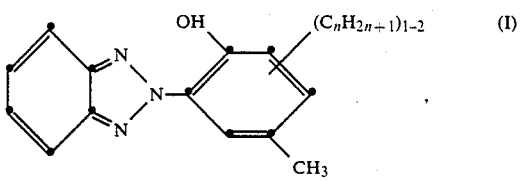

(I)

wherein n is an integer from 8 to 14 and the alkyl radical is a mixture of at least two isometric radicals.

* * * * *